(12) United States Patent
Gobrecht

(10) Patent No.: US 11,441,508 B2
(45) Date of Patent: Sep. 13, 2022

(54) METHOD FOR SENSING A FUEL COMPOSITION TO RESTRICT THE USABILITY OF A VEHICLE IN THE EVENT OF A MISFUELING

(71) Applicant: Volkswagen Aktiengesellschaft, Wolfsburg (DE)

(72) Inventor: Stefan Gobrecht, Isenbuettel (DE)

(73) Assignee: Volkswagen Aktiengesellschaft, Wolfsburg (DE)

( * ) Notice: Subject to any disclaimer, the term of this patent is extended or adjusted under 35 U.S.C. 154(b) by 0 days.

(21) Appl. No.: 17/025,803

(22) Filed: Sep. 18, 2020

(65) Prior Publication Data

US 2021/0079863 A1   Mar. 18, 2021

(30) Foreign Application Priority Data

Sep. 18, 2019   (DE) .................. 10 2019 125 083

(51) Int. Cl.
| | |
|---|---|
| *F02D 41/22* | (2006.01) |
| *B60K 15/03* | (2006.01) |
| *B60K 35/00* | (2006.01) |
| *B60Q 9/00* | (2006.01) |
| *F02D 41/00* | (2006.01) |
| *G01N 33/22* | (2006.01) |

(52) U.S. Cl.
CPC ........ *F02D 41/22* (2013.01); *B60K 15/03006* (2013.01); *B60K 35/00* (2013.01); *B60Q 9/00* (2013.01); *F02D 41/0027* (2013.01); *G01N 33/22* (2013.01); *B60K 2015/0321* (2013.01); *B60K 2015/03309* (2013.01); *B60K 2370/152* (2019.05); *B60K 2370/171* (2019.05); *F02D 2041/224* (2013.01)

(58) Field of Classification Search
CPC .... F02D 41/22; F02D 41/0027; F02D 41/224; B60K 15/03006; B60K 2015/0321; B60K 2015/03309; B60K 35/00; B60K 2370/152; B60K 2370/171; B60Q 9/00; B01N 33/22
USPC ........................................................ 701/102
See application file for complete search history.

(56) References Cited

U.S. PATENT DOCUMENTS

| | | | |
|---|---|---|---|
| 5,701,863 A | 12/1997 | Cemenska et al. | |
| 7,155,334 B1 * | 12/2006 | Stewart ................ | F02D 35/023 |
| | | | 701/114 |
| 7,641,587 B2 | 1/2010 | Jess et al. | |
| 8,191,412 B2 | 6/2012 | Doering | |

(Continued)

FOREIGN PATENT DOCUMENTS

| | | |
|---|---|---|
| DE | 102008014613 A1 | 10/2008 |
| DE | 102008006798 B3 | 8/2009 |

(Continued)

OTHER PUBLICATIONS

"Standard EN 590" published by the European Committee for Standardization, retrieved from Wikipedia on Nov. 4, 2021.

*Primary Examiner* — Robert A Werner
(74) *Attorney, Agent, or Firm* — Muncy, Geissler, Olds & Lowe, P.C.

(57) ABSTRACT

A method for $CO_2$ certification and/or $CO_2$-dependent homologation of vehicles that takes into account at least one design feature of the vehicle, which is characterized in that the detected use of a $CO_2$-reduced fuel is taken into account as a design feature of the vehicle.

11 Claims, 1 Drawing Sheet

(56) References Cited

U.S. PATENT DOCUMENTS

| | | | |
|---|---|---|---|
| 8,897,991 B2 | 11/2014 | Geng et al. | |
| 11,085,383 B2 | 8/2021 | Buerger et al. | |
| 2002/0029770 A1* | 3/2002 | Heffel | F02D 19/029 |
| | | | 123/527 |
| 2016/0194581 A1* | 7/2016 | Phillips | C11C 3/003 |
| | | | 554/167 |
| 2018/0208175 A1* | 7/2018 | Zhang | B60W 10/08 |
| 2018/0216542 A1* | 8/2018 | Athey | F02M 21/0212 |

FOREIGN PATENT DOCUMENTS

| | | |
|---|---|---|
| DE | 102008002356 A1 | 12/2009 |
| DE | 102008002476 A1 | 12/2009 |
| DE | 102008025350 A1 | 12/2009 |
| DE | 102009028321 A1 | 2/2011 |
| DE | 102013215224 A1 | 2/2014 |
| DE | 102012019609 A1 | 4/2014 |
| DE | 102013111520 A1 | 5/2015 |
| DE | 102017203849 A1 | 9/2018 |
| EP | 1847704 A1 | 10/2007 |
| JP | 4083811 B2 | 4/2008 |
| WO | WO2019129858 A1 | 7/2019 |

\* cited by examiner

METHOD FOR SENSING A FUEL COMPOSITION TO RESTRICT THE USABILITY OF A VEHICLE IN THE EVENT OF A MISFUELING

This nonprovisional application claims priority under 35 U.S.C. § 119(a) to German Patent Application No. 10 2019 125 083.8, which was filed in Germany on Sep. 18, 2019, and which is herein incorporated by reference.

BACKGROUND OF THE INVENTION

Field of the Invention

The present invention relates to a method for $CO_2$ certification and/or homologation of vehicles that takes into account at least one design feature of the vehicle.

Description of the Background Art

DE 10 2008 002 476 A1, DE 10 2008 014 613 A1, EP 1 847 704 A1, DE 10 2017 203 849 A1, and DE 10 2009 028 321 A1 are mentioned as prior art, where EP 1 847 704 A1, as the nearest prior art, represents the starting point for the invention. The document EP 1 847 704 A1 describes a method for operating a drive unit that is capable of compensating a deviation in the composition and in a variable fuel quality associated therewith. According to the disclosure, an "aging" of the fuel quality is estimated on a time basis. This deviating quality that is determined is then intended to be taken into account in the process of operating the internal combustion engine.

SUMMARY OF THE INVENTION

It is therefore an object of the present invention to provide a method and an associated system that affect the operation of the vehicle on the basis of a fuel composition. The goal is to more effectively utilize the positive effect of the overall $CO_2$ balance of several fuels in application.

Fuels contain ever-increasing synthetic and biocomponents. One of the important advantages of these fuels is the improved $CO_2$ values of the overall carbon footprint. The applicant's R33 biofuel is mentioned by way of example. R33 BlueDiesel complies with the diesel standard DIN EN 590. The fuel consists of up to one third renewable components and has the potential to save at least 20% $CO_2$ as compared with conventional diesel.

Other $CO_2$-reduced biofuels are also known, such as paraffinic diesel and Sweden Class, which has bioethanol content, as well as diesel fuels to which OME (polyoxymethylene dimethyl ethers) are admixed as an additive.

At present, the advantages that new fuels with improved carbon footprint provide are always distributed over a manufacturer's fleet average fuel economy using allocation formulas.

In other words, the use of a $CO_2$-reduced biofuel is not attributed to the individual vehicle. In a known manner, new vehicles, vehicle components, and vehicle systems must be homologated prior to market introduction in accordance with the applicable standards and regulations of the relevant destination country. In this process, the use of $CO_2$-reduced biofuels, for example, is not taken into account.

The starting point of the invention is a method for $CO_2$ certification and/or $CO_2$-dependent homologation of vehicles that takes into account at least one design feature of the vehicle.

When vehicles suited for the invention are mentioned in the claims and the description, this applies equally to motor vehicles, rail vehicles, aircraft, and watercraft.

Provision is made according to the invention that the detected use of a $CO_2$-reduced fuel is taken into account as a design feature of the vehicle.

In an exemplary embodiment of the invention, provision is made that additional $CO_2$-reducing design features of aerodynamics and/or lightweight construction and/or engine efficiency and/or, in particular, the use of a renewably generated green power content, in particular of a plug-in hybrid vehicle, of the vehicle to be certified and/or to be homologated are detected and are taken into account in the $CO_2$ certification and/or $CO_2$-dependent homologation of the vehicle.

It is proposed preferably that the chemical composition is objectively determined or measured by means of a fuel sensor. In a specific composition, a fuel is identified according to the invention in a type of specific composition pattern, which fuel is considered or defined as a $CO_2$-reduced fuel through comparison with at least one standard specific composition pattern, a so-called reference composition pattern, if the specific composition pattern matches the reference composition pattern, so that non-$CO_2$-reduced fuel can be distinguished from $CO_2$-reduced fuel through the specific chemical composition patterns and through comparison with at least one standard reference composition pattern. Consequently at least one standardized biofuel, preferably multiple standardized biofuels, is/are defined as $CO_2$-reduced fuels that can be recognized/analyzed on the basis of the chemical composition and/or on the basis of markers, wherein this/these standardized biofuel(s) is/are considered and designated as $CO_2$-reduced fuel(s), and each of the $CO_2$-reduced fuels is available as a reference composition pattern for comparison with other fuels.

In particular, the differentiation of a non-$CO_2$-reduced fuel from a $CO_2$-reduced fuel is made on the basis of chemical components of the specific composition pattern, wherein these chemical components are also correspondingly present in the standard reference composition pattern.

The differentiation of a non-$CO_2$-reduced fuel from a $CO_2$-reduced fuel can be made on the basis of at least one marker of the specific composition pattern that is added to a fuel approved as a $CO_2$-reduced fuel, wherein the at least one marker is also correspondingly present in the standard reference composition pattern.

The two embodiments of the method may be combined with one another.

In this regard, a method is preferably proposed in which the chemical components of the fuel or of the at least one marker are detected through an analysis method associated with the at least one fuel sensor that recognizes, by chemical or other means, the chemical components and/or the at least one marker added to the approved fuel, and the specific composition pattern is produced by means of which a conclusion is made about the $CO_2$-reduced fuel through the above-mentioned comparison with the reference composition pattern.

It is a matter of course that legal regulations and standards exist and are consulted that contain or reflect the chemical fuel composition, which is to say the specific reference composition pattern, of established $CO_2$-reduced fuels.

Furthermore, provision is preferably made that a predefinable threshold value of the particular content of the chemical components of the fuel is defined, wherein the threshold value must be exceeded for the fuel to be recognized and classified as $CO_2$-reduced fuel by means of the specific reference composition pattern.

In particular, provision is made that a spectroscopic method, in particular NIR spectroscopy (NIR=near-infrared spectroscopy) or NMR spectroscopy (NMR=nuclear magnetic resonance spectroscopy) or LIF spectroscopy (LIF=laser-induced fluorescence spectroscopy) or TR-LIF spectroscopy (TR-LIF=time-resolved laser-induced fluorescence spectroscopy) is carried out as the analysis method for analyzing the chemical components of the fuel and/or of the at least one marker, with which method is associated a fuel sensor that detects the chemical components of the fuel and of the at least one marker.

Especially when LIF spectroscopy or TR-LIF spectroscopy is carried out, a dilution unit that is not shown in detail in the figure is optionally associated with the fuel sensor inside the fuel supply system in order to dilute the sample to be analyzed, by which means a greater selectivity is achieved in the evaluation of the chemical components of the fuel.

Provision is also made that at least one of the above-mentioned analysis methods or another marker-specific analysis method for analyzing the at least one marker, an analysis method specifically associated with the relevant marker is carried out, with which method is associated a specific fuel sensor that recognizes or detects only the at least one marker in another specific non-chemical manner.

The method is further designed such that a use of solely a $CO_2$-reduced fuel in the vehicle is ensured to the greatest degree possible by the means that a use of the vehicle is permitted only when the $CO_2$-reduced fuel is utilized.

According to the invention, a notification and prompting function is implemented.

The method is characterized, for example, in that in the event that the fuel sensor detects that no $CO_2$-reduced fuel is in the fuel tank and/or in the event that no power with green power content was used at a charging station, a notification concerning the current non-use of $CO_2$-reduced fuel and/or concerning the non-use of power with at least a certain green power content is issued, in particular is issued in graduated fashion, to the user by means of at least one display element, wherein a notification includes at least a message about the misfueling (fuel and/or power) that has occurred and preferably a corresponding prompt for a corrective action.

In other words, the use of charging power with a specific, predefined green power content that is standardized for the vehicle is used for homologation of the vehicle in analogous manner to the fuel standardized as $CO_2$-reduced fuel.

The actions described below are taken, for example, when charging power with the specific, predefined, standardized green power content has not been used and/or when fuel accepted as standardized $CO_2$-reduced fuel has not been used.

According to the invention, an action information function is implemented.

In particular, it is preferably provided as an information action that a) information is provided in the at least one display element of a fuel supply system of the vehicle, in particular in a first level, about a misfueling detected by the fuel sensor, wherein a prompt is issued to visit the nearest repair shop within a predefinable travel distance.

Or it is preferably provided as an information action that b) information is provided in the at least one display element of a fuel supply system of the vehicle, in particular in a second level, about a misfueling detected by the fuel sensor, wherein a prompt is issued to visit the nearest repair shop within a predefinable travel distance, wherein information is additionally provided in the display element of the fuel supply system of the vehicle about restrictive actions to occur in future as a result of the misfueling.

According to the invention an action function is implemented that actively intervenes in certain vehicle parameters without endangering the user of the vehicle.

In a preferred embodiment of the invention, provision is made that actions with graduated effectiveness are initiated with regard to preventing circumvention of the at least one notification, in particular the graduated notifications a), b).

Z1: A limitation of a maximum speed of the vehicle or of a speed of the internal combustion engine and/or Z2: a reduction in the torque of the internal combustion engine and/or Z3: a prevention of a predefinable nth engine start (n=predefinable number of remaining permissible engine starts), wherein n=0 is possible so that even one next engine start is prevented, or Z4: a prevention of a predefinable nth engine start (n=predefinable number of remaining permissible engine starts) in combination with the reaching of a predefined travel distance (x), wherein only n predefinable engine starts (n=predefinable number of remaining permissible engine starts) is/are permitted once the predefined travel distance (x) is reached, wherein n=0 is possible so that even one next engine start is prevented after the predefined travel distance (x) is reached.

According to the invention, an arrangement of a fuel sensor in a fuel supply system of an internal combustion engine for carrying out the method for $CO_2$ certification and/or $CO_2$-dependent homologation of vehicles that takes into account at least one design feature of the vehicle is proposed, wherein provision is made according to the invention that at least the detected use of a $CO_2$-reduced fuel on the basis of a specific composition pattern that has been detected is taken into account as a design feature of the vehicle, wherein the fuel sensor is arranged in the fuel supply system, in particular in a fuel tank or in a fuel feed line, in particular between fuel tank and internal combustion engine, wherein the fuel sensor is equipped to determine the chemical components of the fuel in order to determine specific composition patterns, on the basis of which a differentiation can be made through comparison with the at least one reference composition pattern.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
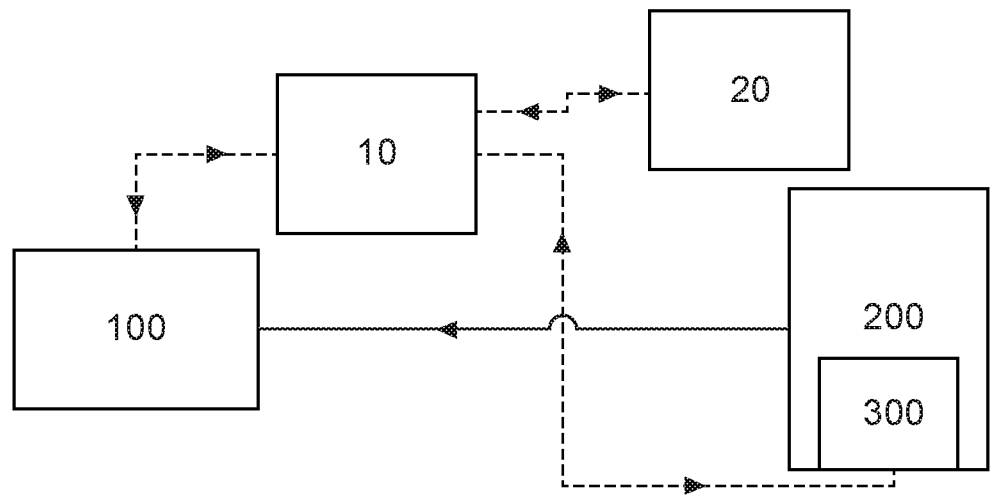
FIG. 1 is a schematic representation to illustrate the flow of material and signals of a vehicle that permits a sensing of the fuel composition and/or of a marker by an associated fuel supply system.
Figure 2:
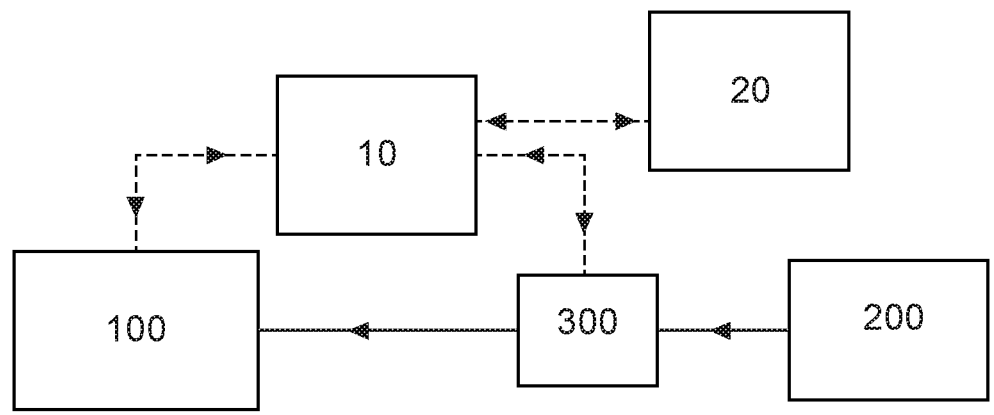
FIG. 2 is a schematic representation to illustrate the flow of material and signals of the vehicle that permits a sensing of the fuel composition and/or of a marker in the associated fuel supply system.

The invention is explained in an overview of FIGS. 1 and 2, with reference accordingly being made in the description to the figures.

The invention is based on the starting point of a fuel supply system with which is associated a suitable control device, in particular an engine control unit 10, and which has a control connection to an internal combustion engine 100 and, according to the invention, to a particular fuel sensor 300.

The fuel supply system includes a fuel tank 200 and the usual additional components that likewise can be controlled by the engine control unit 10; these are not shown in the simplified schematic representations in FIGS. 1 and 2.

In FIG. 1, the fuel sensor 300 is arranged in the fuel tank 200.

In FIG. 2, the fuel sensor 300 is arranged in the fuel feed line between fuel tank 200 and internal combustion engine 100.

Fundamentally, the basic idea is that the fuel sensor 300 has a control connection to the engine control unit 10, wherein the fuel sensor 300 is designed such that it recognizes which fuel is in the fuel tank 200 and is currently being used in operating the internal combustion engine 100.

Provision is made that the signals from the fuel sensor 300 are checked by the engine controller in respect of whether a $CO_2$-reduced fuel for which the vehicle has also been homologated (approved) is in the fuel tank 200.

Provision is made according to the invention that, in the event that the fuel sensor 300 detects that no $CO_2$-reduced fuel is in the fuel tank 200, actions are taken by the engine controller, which are explained below.

a) The user is informed of the misfueling by clear messages in a display element 20 of the fuel supply system of the vehicle and is prompted to visit the nearest repair shop within an additional predefinable travel distance x (x=100 km, for example). At the repair shop, the fuel supply system is cleaned and the vehicle is filled again with the approved $CO_2$-reduced fuel so that operational readiness is reestablished.

If the user does not take the vehicle to the repair shop within the predefined travel distance (100 km, for example), additional actions are taken.

b) The user is informed of the misfueling by clear messages in a display element 20 of the fuel supply system of the vehicle and is informed of restrictive actions as a result of the misfueling, in order to force the user to take the vehicle to the repair shop so that the fuel supply system can be cleaned and the vehicle can be filled again with the approved fuel.

The following coercive actions Zn are proposed:

According to a first action Z1, a limitation of the maximum speed takes place.

According to a second action Z2, a reduction in the torque of the internal combustion engine 100, and thus poor drivability of the vehicle, is brought about.

According to a third action Z3, only n remaining engine starts (n=predefinable number of remaining permissible engine starts) are permitted, wherein n=0 is possible so that even one next engine start is prevented.

According to a fourth action Z4, the third action Z3 is combined with a predefinable remaining permissible travel distance x=km, wherein only n engine starts (n=predefinable number of remaining permissible engine starts) is/are permitted once the predefined travel distance is reached, wherein n=0 is possible so that even one next engine start is prevented.

The fuel sensor 300 and the associated analysis method are designed such that $CO_2$-reduced fuels, in particular synthetic and biocomponents of $CO_2$-reduced fuels, or $CO_2$-reducing additives or $CO_2$-reduced fuels, is possible on the basis of specific markers in the specific composition pattern through comparison with the at least one reference composition pattern standardized or standard as a $CO_2$-reduced fuel.

$CO_2$-reduced fuels: biodiesel (for example the applicant's R33 BlueDiesel), paraffinic diesel, Sweden Class $CO_2$-reducing additives: OME (polyoxymethylene dimethyl ethers), ethanol additives of all types Markers signaling $CO_2$-reduced fuels and/or $CO_2$-reducing additives $CO_2$-reduced fuel with chemical markers or markers that mark through other means It is proposed to use a homologation method in which the $CO_2$ values of a vehicle, in particular of a passenger car or a truck, are identified.

Such a method consists essentially of a calculation tool that is based on computation of components, technical equipment, and design features with relevance for the $CO_2$ emissions of the relevant vehicle (passenger car, truck, and so on).

This calculation tool takes $CO_2$-reducing design features into account for the vehicle, in particular features of aerodynamics, lightweight construction, engine efficiency, and/or the use of a renewably generated green power content of an electrical charging of a plug-in hybrid vehicle, and also the use of a fuel that is classified as a $CO_2$-reduced fuel under a standard, wherein it is substantially ensured in accordance with the inventive method that only $CO_2$-reduced fuel and/or renewably generated green power content of an electrical charging is used.

It is proposed, in particular, to expand the European Commission's VECTO calculation tool (Vehicle Energy Consumption Calculation Tool) currently under development by adding the feature of the use of a $CO_2$-reduced fuel in the vehicle, and to introduce a specific homologation of certain "$CO_2$-reduced vehicles." In this way, an effective contribution can be made to reducing $CO_2$ emissions that takes into account the method according to the invention and the associated system.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for $CO_2$ certification and/or $CO_2$-dependent homologation of a vehicle on the basis of at least one design feature of the vehicle which includes an approved use of a $CO_2$-reduced fuel in the vehicle, the method comprising:

detecting, by at least one fuel sensor arranged in a fuel tank of the vehicle or a fuel feed line that extends between the fuel tank and an internal combustion engine of the vehicle, whether a fuel in the vehicle is a $CO_2$-reduced fuel which is approved for the vehicle or is a non-$CO_2$-reduced fuel which would indicate that a misfueling of the vehicle has occurred; and displaying at least one error notification to a user of the vehicle, via at least one display element in the vehicle, when the at least one fuel sensor detects that the fuel in the vehicle is the non-$CO_2$-reduced fuel so that a corrective action can be undertaken, wherein a specific chemical composition of the fuel is detected by the at least one fuel sensor, wherein a specific chemical composition pattern is created from the specific chemical composition of the fuel and is compared with standard reference composition patterns of $CO_2$-reduced fuels, so that a fuel considered to be $CO_2$-reduced is inferred in the event of a match, wherein the at least one error notification that is displayed includes at least a message about the misfueling that has occurred and a corresponding prompt for the corrective action to be undertaken, the corresponding prompt being a prompt to visit the nearest repair shop within a predefinable travel distance, wherein after issuing the prompt to visit the nearest repair shop, information is additionally provided in the display element about restrictive actions to occur in the future as a result of the misfuelling, wherein the restrictive actions have graduated effectiveness and are initiated to prevent circumvention of the at least one error notification by the user, wherein the restrictive actions, listed in increasing graduated effectiveness, include:

a limitation of a maximum speed of the vehicle or of a speed of the internal combustion engine; and/or a reduction in a torque of the internal combustion engine; and/or a prevention of a predefinable nth engine start (n=predefinable number of remaining permissible engine starts), wherein n=0 is possible so that even one next engine start is prevented, or a prevention of a predefinable nth engine start (n=predefinable number of remaining permissible engine starts) in combination with the reaching of a predefined travel distance, wherein only n predefinable engine starts (n=predefinable number of remaining permissible engine starts) is/are permitted once the predefined travel distance is reached, wherein n=0 is possible so that even one next engine start is prevented after the predefined travel distance is reached.

2. The method according to claim 1, wherein the at least one design feature of the vehicle includes additional features that are detected, the additional features include aerodynamics and/or lightweight construction and/or engine efficiency and/or use of a renewably generated green power content.

3. The method according to claim 1, wherein a differentiation of a non-$CO_2$-reduced fuel from a $CO_2$-reduced fuel is made on the basis of chemical components in the specific chemical composition pattern that have $CO_2$-reducing effects, wherein the chemical components are also contained in the standard reference composition patterns, so that a fuel considered to be $CO_2$-reduced is inferred in the event of a match.

4. The method according to claim 1, wherein a differentiation of a non-$CO_2$-reduced fuel from a $CO_2$-reduced fuel is made on the basis of at least one marker detected in the specific chemical composition pattern that is known to be added to a fuel approved as a $CO_2$-reduced fuel, wherein the at least one marker is also contained in the standard reference composition patterns, so that a fuel considered to be $CO_2$-reduced is inferred in the event of a match.

5. The method according to claim 3, wherein the chemical components of the fuel are detected through an analysis method associated with the at least one fuel sensor that recognizes the chemical components.

6. The method according to claim 5, wherein a predefinable threshold value of the chemical components of the fuel is defined, wherein the threshold value must be exceeded for the fuel to be recognized and classified as $CO_2$-reduced fuel.

7. The method according to claim 5, wherein a spectroscopic method or NIR spectroscopy (NIR=near-infrared) or NMR spectroscopy (NMR=nuclear magnetic resonance) or LIF spectroscopy (LIF=laser-induced fluorescence) or TR-LIF spectroscopy (TR-LIF=time-resolved laser-induced fluorescence) is carried out as the analysis method for analyzing the chemical components of the fuel.

8. The method according to claim 1, wherein the use of a $CO_2$-reduced fuel in the vehicle is ensured by permitting use of the vehicle only when the $CO_2$-reduced fuel is utilized.

9. The method according to claim 4, wherein the at least one marker is detected through an analysis method associated with the at least one fuel sensor that recognizes the at least one marker added to the fuel approved as a $CO_2$-reduced fuel.

10. The method according to claim 9, wherein an analysis method specifically associated with the relevant marker is carried out as the analysis method for analyzing the at least one marker, with which method is associated a specific one of the at least one fuel sensor that detects only the at least one marker.

11. The method according to claim 9, wherein a spectroscopic method or NIR spectroscopy (NIR=near-infrared) or NMR spectroscopy (NMR=nuclear magnetic resonance) or LIF spectroscopy (LIF=laser-induced fluorescence) or TR-LIF spectroscopy (TR-LIF=time-resolved laser-induced fluorescence) is carried out as the analysis method for analyzing the at least one marker.

* * * * *